United States Patent [19]

Kubota et al.

[11] Patent Number: 5,081,260

[45] Date of Patent: Jan. 14, 1992

[54] 3-(2-OXO-1-PYRROLIDINYL)-PROPYLSILANES AND METHOD FOR PREPARING THE SILANE COMPOUNDS

[75] Inventors: Tohru Kubota; Toshinobu Ishihara; Mikio Endo, all of Joetsushi, Japan

[73] Assignee: Shin-Etsu Chemical Co., Ltd., Japan

[21] Appl. No.: 508,570

[22] Filed: Apr. 13, 1990

[30] Foreign Application Priority Data

Apr. 13, 1989 [JP] Japan ................................. 1-91794

[51] Int. Cl.$^5$ ........................... C09K 3/18; C07F 7/18
[52] U.S. Cl. ........................... 548/406; 252/70; 106/13
[58] Field of Search ........................... 548/406

[56] References Cited

U.S. PATENT DOCUMENTS 2,809,958 10/1957 Barnes ..................... 528/326
3,016,366 1/1962 Glickman ................. 528/326

FOREIGN PATENT DOCUMENTS 52-42873 10/1975 Japan .
52-46065 10/1975 Japan .

OTHER PUBLICATIONS

Khananashvili Chemical Abstracts vol. 98 198318z (1982).

Primary Examiner—Mark L. Berch
Attorney, Agent, or Firm—Parkhurst, Wendel & Rossi

[57] ABSTRACT 3-(2-oxo-1-pyrrolidinyl)-propylsilane compounds represented by the following general formula (I) are herein disclosed:

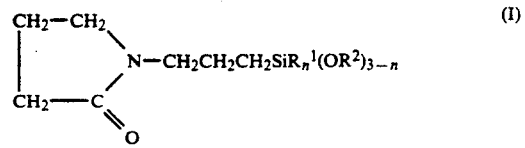

wherein $R^1$ and $R^2$ may be the same or different and each represents a hydrocarbon group having 1 to 4 carbon atoms; and n is an integer ranging from 0 to 2. The propylsilane compounds may be prepared by, for instance, reacting 1-allyl-2-oxopyrrolidine with a hydrogen silane such as trimethoxysilane or trichlorosilane in the presence of a platinum catalyst or further optionally reacting the resulting 3-(2-oxo-1-pyrrolidinyl)-propyl halogenosilane (in the case where a halogenosilane is used) with an alcohol such as methanol. These propylsilane compounds are effective as anti-clouding agent for treating the surface of a variety of substrate.

4 Claims, No Drawings

5,081,260

3-(2-OXO-1-PYRROLIDINYL)-PROPYLSILANES AND METHOD FOR PREPARING THE SILANE COMPOUNDS

BACKGROUND OF THE INVENTION

The present invention relates to novel silane compounds and more particularly to novel silane compounds which are useful as surface treating agents for imparting anti-clouding properties to the surface of a variety of substances as well as a method for preparing such silane compounds.

Alkoxysilane compounds having functional organic groups have widely been used as surface treating agents which can immobilize their functional organic groups on the surface of various substances or substrates to thus impart various excellent properties to the surface of the substrates. For instance, $(CH_3O)_3Si(CH_2)_{17}CH_3$ is effective as an agent for making the surface of an inorganic substance hydrophobic and has been employed as an agent for processing carriers for liquid chromatography and gas chromatography.

In addition, $(CH_3O)_3SiCH_2CH_2(CF_2)_7CF_3$ can form a low energy surface on substrates and thus has been used as a water repellency agent and oil repellency agent or a releasing agent.

The silane compounds can also be used as anti-clouding agents for the transparent surface of substrates such as glass substrates.

SUMMARY OF THE INVENTION

Accordingly, an object of the present invention is to provide a novel organic silane compound which is useful as a surface treating agent for imparting semipermanent anti-clouding properties to the surface of a variety of substrates.

Another object of the present invention is to provide a novel organic silane compound which exhibits effects of enhancing miscibility, adhesion and heat resistance of a variety of materials.

A further object of the present invention is to provide a method for preparing such a novel organic silane compound.

The inventors of this invention have conducted various studies to achieve the foregoing objects of the present invention, have taken note of the fact that silane compounds having hydrophilic groups would impart anti-clouding properties to the surface of a substrate and thus have synthesized and investigated various silane compounds having hydrophilic groups. As a result, the inventors have completed the present invention.

The present invention, therefore, relates to 3-(2-oxo-1-pyrrolidinyl)-propylsilane compounds represented by the following general formula (I):

$$\begin{array}{c} CH_2-CH_2 \\ | \quad\quad\quad \backslash \\ | \quad\quad\quad\quad N-CH_2CH_2CH_2SiR^1_n(OR^2)_{3-n} \\ CH_2-C \quad / \\ \quad\quad \backslash\!\!\!_O \end{array} \quad (I)$$

wherein $R^1$ and $R^2$ may be the same or different and each represents a saturated or unsaturated, linear or branched, hydrocarbon group having 1 to 4 carbon atoms; and n is an integer ranging from 0 to 2. These silane compounds of the present invention exhibit various excellent effects of improving surface properties of different substrates, in particular, they are effective to impart anti-clouding properties to the surface of such substrates.

DETAILED EXPLANATION OF THE INVENTION

The present invention will be explained in more detail below.

In the general formula (I), the hydrocarbon group $R^1$ and $R^2$ may be alkyl groups such as methyl, ethyl, n-propyl, isopropyl, n-butyl, isobutyl, t-butyl.

Specific examples of the novel compounds of the present invention, i.e., the 3-(2-oxo-1-pyrrolidinyl)-propylsilane compounds include 3-(2-oxo-1-pyrrolidinyl)-propyltrimethoxysilane,
3-(2-oxo-1-pyrrolidinyl)-propylmethyldimethoxysilane,
3-(2-oxo-1-pyrrolidinyl)-propylmethyldiethoxysilane,
3-(2-oxo-1-pyrrolidinyl)-propylethyldiethoxysilane,
3-(2-oxo-1-pyrrolidinyl)-propyldimethylbutoxysilane.

The novel 3-(2-oxo-1-pyrrolidinyl)-propylsilane compounds of the present invention can be prepared according to either of the following two methods:

One method comprises subjecting, to hydrosililation, 1-allyl-2-oxopyrrolidine represented by the following formula (II):

$$\begin{array}{c} CH_2-CH_2 \\ | \quad\quad\quad \backslash \\ | \quad\quad\quad\quad N-CH_2CH=CH_2 \\ CH_2-C \quad / \\ \quad\quad \backslash\!\!\!_O \end{array} \quad (II)$$

and a hydrogen silane represented by the following general formula (III):

$$HSiR^1_n(OR^2)_{3-n} \quad (III)$$

in the presence of a platinum catalyst to thus give 3-(2-oxo-1-pyrrolidinyl)-propylsilane represented by the general formula (I):

In the foregoing general formula (III), $R^1$ and $R^2$ are the same as those defined above in connection with the general formula (I). Preferable examples of $R^1$ and $R^2$ are methyl, ethyl, n-propyl, isopropyl and butyl groups.

In addition, specific examples of the hydrogen silanes represented by the general formula (III) include alkoxysilane compounds such as trimethoxysilane, methyldiethoxysilane, ethyldiethoxysilane and dimethylbutoxysilane.

This method for preparation, it is desirable to employ a reactor equipped with a stirrer, a thermometer, a reflux condenser and a dropping funnel.

The amount of the platinum catalyst ranges from 10 to 500 ppm on the basis of the amount of 1-allyl-2-oxopyrrolidine. Examples of the platinum catalysts which may be used in the present invention are $H_2PtCl_6$.

The hydrogen silanes represented by the general formula (III) are dropwise added in an amount ranging from 1 to 1.5 equivalent with respect to the amount of 1-allyl-2-oxopyrrolidine represented by the general formula (II) and the reaction is preferably carried out at a temperature ranging from 50° to 150° C.

The other method comprises (i) subjecting, to hydrosililation, 1-allyl-2-oxopyrrolidine represented by the following formula (II):

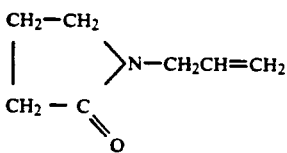

(II)

and a hydrogen silane represented by the following general formula (IV):

$$HSiR^1_nX_{3-n} \quad (IV)$$

in the presence of a platinum catalyst to thus give a 3-(2-oxo-1-pyrrolidinyl)-propylhalogenosilane compound represented by the following general formula (V):

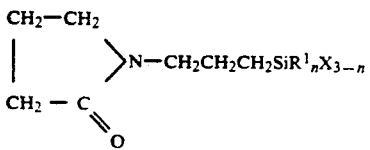

(V)

and then (ii) reacting the resulting propylhalogenosilane compound with an alcohol represented by the following general formula (VI):

$$R^2OH \quad (VI)$$

to thus obtain a 3-(2-oxo-1-pyrrolidinyl)-propylsilane compound represented by the general formula (I).

In the foregoing general formulae (V) and (VI), $R^1$ and $R^2$ are the same as those defined above in connection with the general formula (I). Preferable examples of $R_1$ and $R_2$ are methyl, ethyl, n-propyl, isopropyl and butyl groups. In the foregoing general formula (V), X represents a halogen atom such as fluorine, chlorine, bromine or iodine atom; and n is likewise the same as that defined above.

In addition, specific examples of the hydrogen silanes represented by the general formula (IV) include chlorosilane compounds such as trichlorosilane, methyldichlorosilane, butyldichlorosilane and dimethylchlorosilane.

Specific examples of the alcohols represented by the general formula (VI) and useful in the method of the present invention include methanol, ethanol, propanol, isopropanol and butanol.

In this method for preparation, it is desirable to employ a reactor equipped with a stirrer, a thermometer, a reflux condenser and a dropping funnel.

The amount of the platinum catalyst ranges from 10 to 500 ppm on the basis of the amount of 1-allyl-2-oxopyrrolidine. Examples of the platinum catalysts which may be used in the present invention are $H_2PtCl_6$.

The hydrogen silanes represented by the general formula (IV) are dropwise added in an amount ranging from 1 to 1.5 equivalent with respect to the amount of 1-allyl-2-oxypyrrolidine shown by general formula (II) and the reaction is preferably carried out at a temperature ranging from 50° to 150° C.

It is preferable in the second method that after the dropwise addition of the hydrogen silane, a tertiary amine and an aprotic reaction solvent be added in an amount ranging from 1 to 1.5 eq. with respect to the halogen atom of the hydrogen silane. Examples of such tertiary amines are triethylamine and N,N-dimethylaniline and those of the aprotic reaction solvents are toluene, xylene, hexane and tetrahydrofuran.

The amount of the alcohol represented by the general formula (VI) ranges from 1 to 1.5 eq. with respect to the halogen atom present in the 3-(2-oxo-1-pyrrolidinyl)-propylhalogenosilane of the general formula (V).

As has been described above in detail, the method according to the present invention makes it possible to provide 3-(2-oxo-1-pyrrolidinyl)-propylisilane compounds useful as surface treating agents for imparting various excellent properties to the surface of a variety of substrates.

Moreover, the novel substances of the present invention, i.e., 3-(2-oxo-1-pyrrolidinyl)-propylsilane compounds useful as surface treating agents for imparting semipermanent anti-clouding properties to the surface of a variety of substrates. When the transparent surface of substrates such as glass is treated with the compound of this invention, not only the surface of the substrate is protected, but also it can impart high anti-clouding properties to the surface.

In addition, these compounds are also effective as coupling agents for improving miscibility, adhesion or the like between inorganic materials such as silane, glass fibers or asbestos and organic polymers such as polyamides and epoxy resins.

Further, the compounds of the present invention can be used as copolymerizable components for manufacturing nylons and they make it possible to improve the properties of nylons, in particular heat resistance and strength thereof since they contain a cyclic amido group, i.e., 2-oxo-1-pyrrolidinyl groups.

The present invention will hereunder be explained in more detail with reference to the following non-limitative working Examples and Reference Examples.

REFERENCE EXAMPLE:

Preparation of 1-Allyl-2-Oxopyrrolidine

To a 5 liter volume flask of glass equipped with a stirrer, a fractional distillation column, a thermometer and a dropping funnel, there were added 270.1 g (5.0 mol) of sodium methoxide and 2 liters of toluene. After 425.6 g (5.0 mol) of 2-pyrrolidone was dropwise added to the flask through the dropping funnel at room temperature, the resulting methanol was completely removed by the fractional distillation column. 6.9 g (25 mmol) of (Butyl-)$_4$NCl was added as a phase transfer catalyst and 382.7 g (5.0 mol) of allyl chloride was dropwise added to the reaction mixture at a temperature ranging from 60° to 70° C. through the dropping funnel to react them. After the completion of the reaction, water was added to dissolve salts formed during the reaction and then the organic phase was removed. Then the organic phase was distilled to separate the fractions having a boiling point ranging from 75° to 76° C./4 mmHg. Thus, 562.5 g of 1-allyl-2-oxopyrrolidine was obtained in a yield of 89.9%.

EXAMPLE 1

Preparation of 3-(2-Oxo-1-Pyrrolidinyl)-Propyltrimethoxysilane

To a 500 ml volume glass flask equipped with a stirrer, a reflux condenser, a thermometer and a dropping funnel, there were added 125.2 g (1.0 mol) of 1-allyl-2- oxopyrrolidine and 0.5 g of 4% isopropyl alcohol solution of $H_2PtCl_6$. Trimethoxysilane (122.2 g; 1.0 mol) was dropwise added through the dropping funnel at a temperature ranging from 100° to 110° C. over 2 hours and the reaction mixture was allowed to stand at 100° C. for 30 minutes. The reaction solution was distilled to give 183.8 g of a compound having a boiling point of 123° to 125° C./2 mmHg in an yield of 74.3%.

The compound was analyzed by mass spectroscopy (MS), NMR spectroscopy and IR spectroscopy and the results observed were listed below.

* Mass Spectra (MS): m/z (ratio of spectral intencity) 247(4), 232(2), 218(14), 215(60), 200(14), 174(22), 121(100), 112(21), 98(86), 91(66), 70(63).

* NMR Spectra: δ (ppm)

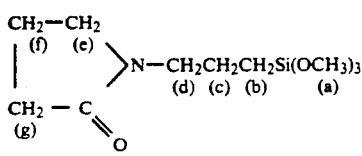

a: 3.51(S); b: 0.55(M); c: 1.57(M); d: 3.21(T); e: 3.32(T); f: 1.46(M); g: 2.33(T).

* IR Spectra: ($cm^{-1}$) 2920, 2820, 1680, 1490, 1460, 1420, 1310, 1280, 1265, 1185, 1080, 960, 810.

On the basis of the foregoing results, it was confirmed that the resulting product was a compound represented by the following formula:

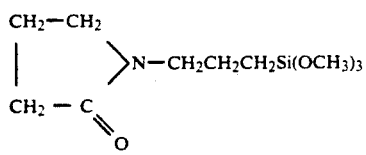

EXAMPLE 2

Preparation of 3-(2-Oxo-1-Pyrolidinyl)-Propylmethyldiethoxysilane

The same procedures used in Example 1 were repeated except that 134.3 g (1.0 mol) of methyldiethoxysilane was substituted for 122.2 g (1.0 mol) of trimethoxysilane and thus 197.4 g of a compound having a boiling point of 122° to 124° C./1 mmHg was obtained. The yield of the compound was 76.1%.

The compound was likewise analyzed by mass spectroscopy (MS), NMR spectroscopy and IR spectroscopy and the results observed were listed below.

* Mass Spectra (MS): m/z (ratio of spectral intencity) 259(7), 244(22), 230(47), 214(43), 213(71), 202(23), 198(23), 172(28), 133(100), 98(47), 89(33), 77(66).

* NMR Spectra: δ (ppm)

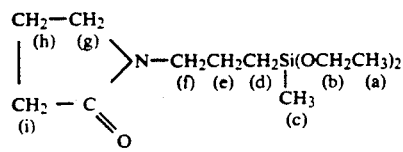

a: 1.16(T); b: 3.70(Q); c: 0.07(S); d: 0.52(M); e: 1.53(M); f: 3.21(T); g: 3.33(T); h: 1.96(M); i: 2.33(T).

* IR Spectra: ($cm^{-1}$) 2960, 2920, 2870, 1880, 1495, 1460, 1430, 1390, 1310, 1285, 1260, 1230, 1165, 1105, 1075, 945, 870, 820.

On the basis of the foregoing results, it was confirmed that the resulting product was a compound represented by the following formula:

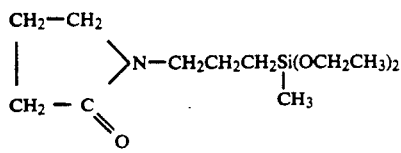

EXAMPLE 3

Preparation of 3-(2-Oxo-1-Pyrrolidinyl)-Propylmethyldiethoxysilane

To a 500 ml volume glass flask equipped with a stirrer, a reflux condenser, a thermometer and a dropping funnel, there were added 25.0 g (0.2 mol) of 1-allyl-2-oxopyrrolidine and 0.1 g of 4 % isoproply alcohol solution of $H_2PtCl_6$. Methyldichlorosilane (23.0 g; 0.2 mol) was dropwise added through the dropping funnel at a temperature ranging from 100° to 110° C. over 30 minutes and the reaction mixture was allowed to stand at 100° C. for 30 minutes. 150 ml of toluene and 40.5 g (0.4 mol) of triethylamine were added to the reaction solution and then ethanol 18.0 g (0.4 mol) was dropwise added thereinto at room temperature. Resulted salts were filtered out away from the reaction solution. The remained reaction solution was distilled to give 28.5 g of a compound having a boiling point of 122° to 124° C./1 mmHg in an yield of 55.0 %.

The compound was analyzed by mass spectroscopy (MS), NMR spectroscopy and IR spectroscopy so that it was confirmed the same as Example 2 compound.

What is claimed is:

1. A 3-(2-oxo-1-pyrrolidinyl)-propylsilane compound represented by the formula (I):

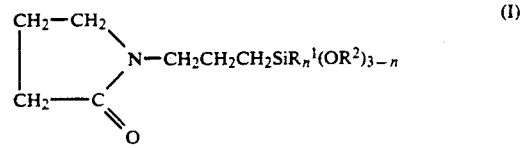

wherein $R^1$ and $R^2$ may be the same or different and each represents a saturated or unsaturated, linear or branched, or cyclic hydrocarbon group having up to 4 carbon atoms; and n is an integer ranging from 0 to 2.

2. The 3-(2-oxo-1-pyrrolidinyl)-propylsilane compound as set forth in claim 1 wherein $R^2$ is a methyl group and n is 0.

3. The 3-(2-oxo-1-pyrrolidinyl)-propylsilane compound as set forth in claim 1 wherein $R^1$ is a methyl group, $R^2$ is an ethyl group and n is 1.

4. The 3-(2-oxo-1-pyrrolidinyl)-propylsilane compound as set forth in claim 1 wherein it is a member selected from the group consisting of:
3-(2-oxo-1-pyrrolidinyl)-propyltrimethoxysilane,
3-(2-oxo-1-pyrrolidinyl)-propylmethyldimethoxysilane,
3-(2-oxo-1-pyrrolidinyl)-propylmethyldiethoxysilane,
3-(2-oxo-1-pyrrolidinyl)-propylethyldiethoxysilane and
3-(2-oxo-1-pyrrolidinyl)-propyldimethylbutoxysilane.

* * * * *